(12) United States Patent
Eckert

(10) Patent No.: US 7,392,709 B2
(45) Date of Patent: Jul. 1, 2008

(54) INLINE MEASURING DEVICE WITH A VIBRATION-TYPE MEASUREMENT PICKUP

(75) Inventor: Gerhard Eckert, Rheinfelden (DE)

(73) Assignee: Endress + Hauser Flowtec AG, Reinach (CH)

( * ) Notice: Subject to any disclaimer, the term of this patent is extended or adjusted under 35 U.S.C. 154(b) by 32 days.

(21) Appl. No.: 11/434,225

(22) Filed: May 16, 2006

(65) Prior Publication Data
US 2006/0266129 A1 Nov. 30, 2006

Related U.S. Application Data

(60) Provisional application No. 60/682,377, filed on May 19, 2005.

(30) Foreign Application Priority Data
May 16, 2005 (DE) .................. 10 2005 023 215

(51) Int. Cl.
*G01F 1/84* (2006.01)
(52) U.S. Cl. .................................. 73/861.355
(58) Field of Classification Search ..............................
73/861.355–861.357
See application file for complete search history.

(56) References Cited

U.S. PATENT DOCUMENTS

| | | | | |
|---|---|---|---|---|
| 5,301,557 | A * | 4/1994 | Cage et al. ............. | 73/861.355 |
| 5,576,500 | A * | 11/1996 | Cage et al. ............. | 73/861.357 |
| 5,594,180 | A | 1/1997 | Carpenter | |
| 6,606,917 | B2 | 8/2003 | Sund | |
| 7,216,549 | B2 * | 5/2007 | Rieder et al. ........... | 73/861.355 |
| 2003/0097884 | A1 | 5/2003 | Sund | |
| 2003/0098069 | A1 | 5/2003 | Sund | |
| 2003/0140712 | A1 | 7/2003 | Barger | |
| 2005/0035867 | A1 | 2/2005 | Matt | |
| 2005/0160787 | A1 | 7/2005 | Bitto | |
| 2005/0284210 | A1 | 12/2005 | Schmidt | |

(Continued)

FOREIGN PATENT DOCUMENTS

DE 10 2004 018 326 A1 3/2005

(Continued)

OTHER PUBLICATIONS

US 6,044,715, 04/2000, Ollila et al. (withdrawn)*

*Primary Examiner*—Harshad Patel
(74) *Attorney, Agent, or Firm*—Bacon & Thomas, PLLC

(57) ABSTRACT

An inline measuring device serves for measuring a medium, especially a gaseous and/or liquid medium, in a pipeline. It includes, a vibration-type measurement pickup and a measuring device electronics electrically coupled with the measurement pickup. The measurement pickup has at least one measuring tube vibrating during operation and communicating with the pipeline, an electromechanical, especially electrodynamic, exciter mechanism acting on the at least one measuring tube for producing and maintaining mechanical oscillations of the measuring tube, a sensor arrangement for producing at least one oscillation measurement signal representing oscillations of the measuring tube and having at least one oscillation sensor arranged on the measuring tube or in its vicinity, and a measurement pickup housing. In an inline measuring device of the invention, it is additionally provided that the measuring device electronics monitors a static internal pressure within the measurement pickup housing and/or a hermeticity of the at least one measuring tube.

41 Claims, 8 Drawing Sheets

U.S. PATENT DOCUMENTS

2006/0005957 A1  1/2006  Moser
2006/0016273 A1  1/2006  Bitto

FOREIGN PATENT DOCUMENTS

DE      1005056164 A  *  5/2007
EP         1 464 923 A1    10/2004
WO    WO 2005/100930 A1  10/2005

* cited by examiner

INLINE MEASURING DEVICE WITH A VIBRATION-TYPE MEASUREMENT PICKUP

FIELD OF THE INVENTION

The invention relates to an inline measuring device for measuring a medium, especially a gaseous and/or liquid medium, flowing in a pipeline.

BACKGROUND OF THE INVENTION

In process and automation technology, physical parameters, such as e.g. mass flow rate, density and/or viscosity, of a medium flowing in a pipeline are often measured using inline measuring devices, which, by means of a vibration-type measurement pickup flowed-through by the medium and a measuring and operating circuit connected thereto, bring about, in the medium, reaction forces, such as e.g. Coriolis forces corresponding with the mass flow rate, inertial forces corresponding with the density of the medium and/or frictional forces corresponding with the viscosity of the medium, etc. and produce, derived from these, a measurement signal representing the current mass flow rate, the current viscosity and/or the current density of the medium.

Such measurement pickups, especially such as are embodied as Coriolis mass flow meters or Coriolis mass flow/density pickups, are described extensively and in detail e.g. in WO-A 04/099735, WO-A 04/038341, WO-A 03/076879, WO-A 03/027616, WO-A 03/021202, WO-A 01/33174, WO-A 00/571/41, WO-A 98/07009, U.S. Pat. Nos. 6,880,410, 6,851,323, 6,807,866, 6,711,958, 6,666,098, 6,308,580, 6,092,429, 5,796,011, 6,006,609, 5,602,345, 5,301,557, 4,876,898, 4,793,191, EP-A 553 939, EP-A 1 001 254, EP-A 1 248 084, EP-A 1 448 956, or EP-A 1 421 349. For conveying the, at least at times, flowing medium, the measurement pickups include at least one pickup tube held appropriately oscillatably in a, most often, thicker, especially tubular and/or beam-like, support cylinder, or in a support frame. In addition, these measurement pickups have a second pickup tube, mechanically coupled with the first pickup tube at least by means of two, especially, however, four, coupling elements (also called node plates, or couplers) and likewise vibrating, at least at times, wherein at last the first pickup tube is embodied as a first measuring tube communicating with the pipeline and serving to convey the medium to be measured. For producing the aforementioned reaction forces, the two pickup tubes are caused to vibrate during operation, driven by a, most often, electrodynamic exciter mechanism, with the two pickup tubes executing, at least at times, bending oscillations about an imaginary oscillation axis essentially parallel to a longitudinal axis of the measurement pickup. For registering vibrations, especially inlet-end and outlet-end vibrations, of the pickup tube and for producing at least one oscillation measurement signal representing the vibrations, such measurement pickups have, additionally, in each case, a sensor arrangement reacting to movements, and, to such extent, also to mechanical oscillations, of the pickup tube.

During operation, the measurement-pickup inner oscillation system, formed by the at least one pickup tube embodied as measuring tube, the medium conveyed at least instantaneously therein, and, at least partly, by the exciter mechanism and the sensor arrangement, is excited by means of the electromechanical exciter mechanism to oscillate mechanically, at least at times, in a wanted oscillation mode at at least one, dominating, wanted oscillation frequency. These oscillations in the so-called wanted oscillation mode are, most often, and especially in the case of use of the measurement pickup as a Coriolis mass flow- and/or density-meter, developed, at least partially, as lateral oscillations. Selected as the wanted oscillation frequency is, in such case, usually a natural, instantaneous resonance frequency of the inner oscillation system, which, in turn, depends both on the size, the shape and the material of the pickup tube and also on an instantaneous density of the medium; under the right circumstances, the wanted oscillation frequency can also be influenced significantly by an instantaneous viscosity of the medium. As a result of fluctuating density of the medium to be measured and/or as a result of medium change produced during operation, the wanted oscillation frequency is naturally changeable during operation of the measurement pickup, at least within a calibrated and, to such extent, predetermined, wanted frequency band, which has, correspondingly, a predetermined lower limit frequency and a predetermined upper limit frequency.

The inner oscillation system of the measurement pickup formed in common by the least one pickup tube, the exciter mechanism and the sensor arrangement is, additionally, usually housed by a pickup housing including, as an integral component thereof, the support frame, or support cylinder, as the case may be. The pickup housing is mechanically coupled with the pipeline via an inlet end and an outlet end. Pickup housings appropriately suited for vibration-type measurement pickups are described, for example, in WO-A 03/076879, WO-A 03/021202, WO-A 01/65213, WO-A 00/57141, U.S. Pat. Nos. 6,776,052, 6,711,958, 6,044,715, 5,301,557, and EP-A 1 001 254. Especially in the case of measurement pickups with bent pickup tubes, the pickup housing has a housing cap connected with the support frame, especially welded therewith. The housing cap surrounds the pickup tube, at least partially.

The measurement pickup housing serves, besides holding the at least one measuring tube, especially also for protecting the measuring tube, the exciter mechanism and the sensor arrangement, as well as other internal components, from external, environmental influences, such as e.g. dust or water spray. Examples of corresponding housing caps for a vibration-type measurement pickup for housing at least one bent tube segment, which, as part of a fluid-conveying measuring tube, vibrates during operation of the measurement pickup, are described e.g. in WO-A 03/021202, WO-A 03/021203, WO-A 00/57141, U.S. Pat. No. 5,301,557, and EP-A 1 001 254.

Users frequently demand of such housings that, in the case of an unsealed or bursting measuring tube, they withstand, leak-free, at least for a specified period of time, the static internal pressure, which then, most often, lies distinctly above the external pressure; compare, in this connection, also WO-A 00/57 141, U.S. Pat. Nos. 6,044,715, 5,301,557, or EP-A 1 001 254. At least for applications with toxic or easily ignitable fluids, the measurement pickup housing must also, in certain circumstances, be able to fulfill the requirements for a safety container. A problem associated therewith is, however, especially for applications with media under high static pressure of over 100 bar, that, after the measuring tube has become unsealed and, therefore, the measurement pickup housing is, under the right circumstances, loaded with an increased internal pressure, an explosion of the measurement pickup housing and/or an electronics housing appropriately affixed to the measurement pickup housing for the measuring device electronics can unexpectedly occur, which, while delayed, is nevertheless just as devastating in effect. This can especially occur, when the pipeline conveying the medium is loaded with unpredictably high pressures and/or with a series of pressure shocks of unpredictably high frequency and/or repetition rate. Beyond this, the measuring tube and measurement pickup housing can also fail due to material flaws and/or fatigue, even after long periods of operation, at pressure values which are really quite within specifications.

On the other hand, it is oftentimes not possible, especially in the case of environmentally endangering media, for example highly toxic and/or highly explosive substances, to use otherwise appropriate safety outlets, such as e.g. burst disks and/or excess pressure valves, for reducing possible excess pressures in the measurement pickup, since a contamination of the environment with the medium must, most often, be prevented with certainty.

SUMMARY OF THE INVENTION

On the basis of the above, it is, therefore, an object of the invention to improve an inline measuring device of the described kind by providing failure recognition of the measuring tube as early as possible, so that unexpected explosions of the inline measuring device, especially of the measurement pickup housing and/or the electronics housing affixed thereto, can be prevented.

For achieving the object, the invention resides in an inline measuring device for measuring a medium, especially a gaseous and/or liquid medium, flowing in a pipeline. Included in the inline measuring device are a vibration-type measurement pickup and measuring device electronics electrically coupled with the measurement pickup. The measurement pickup comprises: At least one measuring tube communicating with the pipeline and vibrating during operation; an electromechanical, especially electrodynamic, exciter mechanism acting on the at least one measuring tube for producing and maintaining mechanical oscillations of the measuring tube; a sensor arrangement for producing, using at least one oscillation sensor arranged on at least one measuring tube or in its vicinity, at least one oscillation measurement signal representing oscillations of the measuring tube; and a measurement pickup housing housing the at least one measuring tube, together with the exciter mechanism and the sensor arrangement. Beyond this, the measuring device electronics monitors a static interior pressure within the measurement pickup housing and/or a hermeticity of the at least one measuring tube.

Additionally, the invention resides in a method for monitoring an inline measuring device for measuring a medium, especially a gaseous and/or liquid medium, flowing in a pipeline. The inline measuring device includes measuring device electronics, as well as a vibration-type measurement pickup electrically coupled with the measuring device electronics. The measurement pickup comprises: At least one measuring tube communicating with the pipeline and vibrating during operation; an electromechanical, especially electrodynamic, exciter mechanism acting on the at least one measuring tube for producing and maintaining mechanical oscillations of the at least one measuring tube; a sensor arrangement for producing at least one oscillation measurement signal representing oscillations of the measuring tube, using at least one oscillation sensor arranged on the measuring tube or in its vicinity; and a measurement pickup housing housing the at least one measuring tube, together with the exciter mechanism and the sensor arrangement. Such method includes the following steps:

allowing the medium to be measured to flow through the at least one measuring tube of the measurement pickup;

causing an exciter current delivered by the measuring device electronics to flow through the exciter mechanism and allowing the at least one measuring tube to vibrate for producing in the medium reaction forces corresponding with at least one measured variable to be registered for the medium;

registering vibrations of the at least one measuring tube by means of the sensor arrangement and producing at least one oscillation measurement signal representing mechanical oscillations of the measuring tube; and determining a static internal pressure within the measurement pickup housing and/or a hermeticity of the at least one measuring tube, wherein the measuring device electronics.

A basic idea of the invention is to recognize possible leaks in the measuring tube and the potential endangering of the environment of the inline measuring device associated therewith by using the driver signal effecting the oscillations and/or by using the oscillation measurement signal representing oscillations of the measuring tube to recognize directly, changes in the oscillatory behavior of the at least one measuring tube brought about by the increased static internal pressure in the measurement pickup housing. An advantage of the invention is that, therefore, additional pressure sensors are not absolutely necessary for monitoring the internal pressure of the measurement pickup housing and/or of the measuring tube.

BRIEF DESCRIPTION OF THE DRAWINGS

The invention will now be explained in greater detail on the basis of the figures of the drawing, in which a preferred example of an embodiment is illustrated. Functionally equal parts are provided in the separate figures with the same reference characters, which, however, are then only repeated in subsequent figures, when such seems helpful.

DESCRIPTION OF THE PREFERRED EMBODIMENTS

Figure 1:
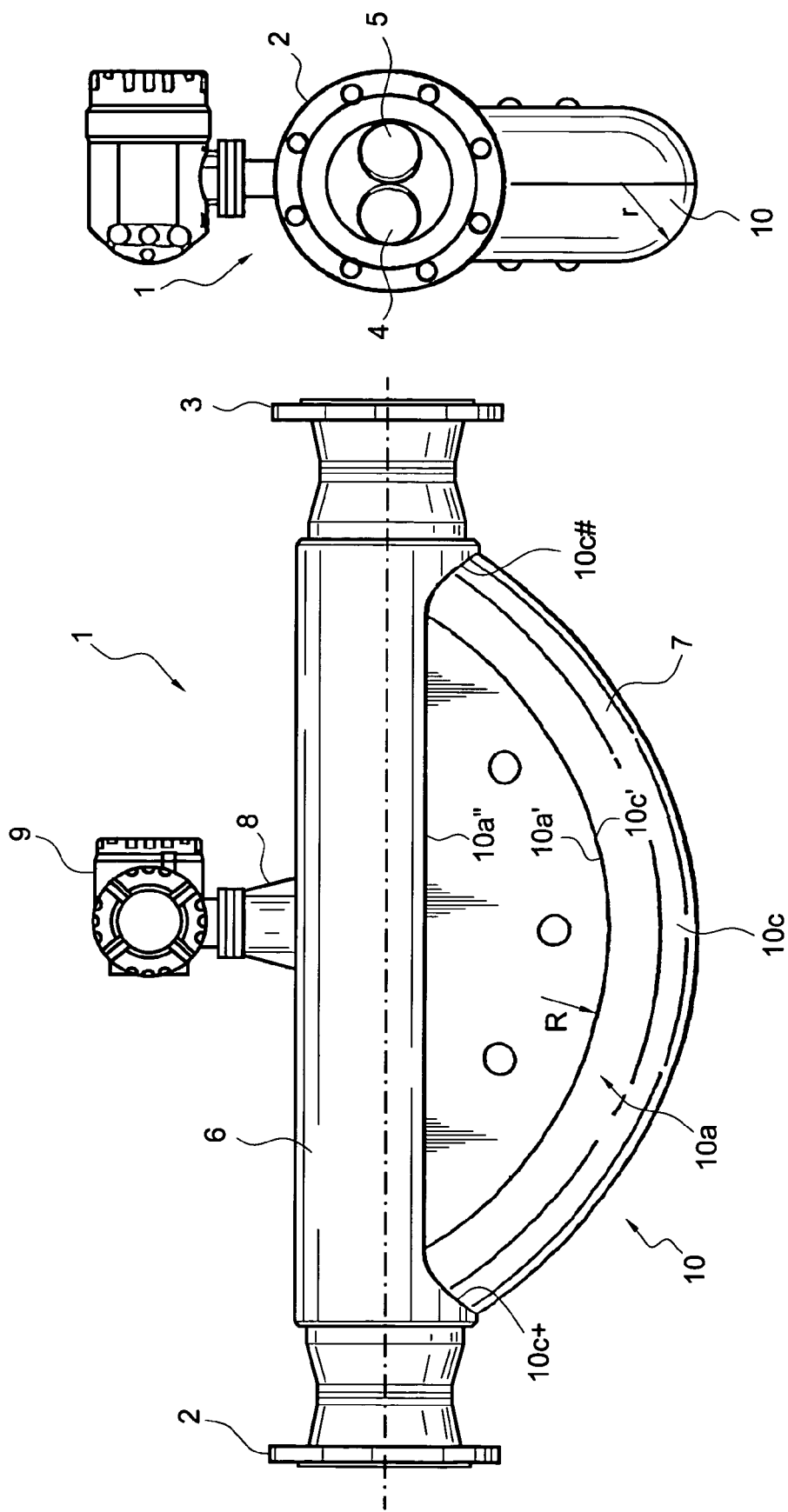
FIGS. 1a, 1b show, in different side views, an inline measuring device, for example one serving as a Coriolis mass flow/density and/or viscosity meter, including a vibration-type measurement pickup.

In a first embodiment of the inline measuring device of the invention, the measuring device electronics uses at least one operating parameter determined internally and/or measured internally during operation to generate repeatedly at least one monitoring value, whose level depends on the instantaneous static internal pressure within the measurement pickup housing and/or on a medium instantaneously surrounding the at least one measuring tube.

In a second embodiment of the inline measuring device of the invention, the measuring device electronics generates the monitoring value from the at least one oscillation measurement signal.

In a third embodiment of the inline measuring device of the invention, the measuring device electronics produces at least one driver signal for the exciter mechanism and the measuring device electronics generates the monitoring value from the at least one driver signal, especially on the basis of the exciter current flowing in the exciter mechanism.

In a fourth embodiment of the inline measuring device of the invention, the exciter current, driven by the measuring device electronics, flows through the exciter arrangement, at least at times, and the measuring device electronics generates the monitoring value on the basis of the exciter current and/or on the basis of a change of the exciter current with respect to time. In a further development of this embodiment of the invention, the measuring device electronics determines an exciter current value, especially a digital exciter current value, which represents instantaneously an electrical current level of the exciter current, and the measuring device electronics generates the monitoring value from at least one internally determined exciter current value, especially on the basis of a series of exciter current values. In another further development of this embodiment of the invention, the measuring device electronics generates the monitoring value on the basis of a series of exciter current values, especially a series of digitally stored exciter current values. Further, it is provided that the measuring device electronics generates the monitoring value on the basis of a time derivative of the electrical current level of the exciter current and/or another measured variable characterizing changes, with respect to time, of the electrical current level of the exciter current.

In a fifth embodiment of the inline measuring device of the invention, the inline measuring device is additionally provided for, and capable of, measuring the density of the medium. In a further development of this embodiment of the invention, the measuring device electronics uses the at least one oscillation measurement signal to determine repeatedly a density measured value, especially a digital density measured value, which represents instantaneously a density of the medium, and the measuring device electronics generates the monitoring value from at least one internally determined density measured value, especially on the basis of a series of density measured values. In a further development of this embodiment of the invention, the measuring device electronics generates the monitoring value on the basis of a series of density measured values, especially digitally stored, density measured values. In another further development of this embodiment of the invention, the measuring device electronics generates the monitoring value on the basis of a time derivative of the measured density and/or another measured variable characterizing time changes of the measured density. Additionally provided is that the measuring device electronics determines the density measured value on the basis of the at least one oscillation frequency serving for the monitoring.

In a sixth embodiment of the inline measuring device of the invention, an exciter current driven by the measuring device electronics flows, at least at times, through the exciter mechanism, the measuring device electronics uses the at least one oscillation measurement signal to determine repeatedly a density measured value, especially a digital density measured value, which represents instantaneously a density of the medium, and the measuring device electronics generates the monitoring value on the basis of a quotient, which is formed by means of an internally determined exciter current value instantaneously representing the exciter current and an internally determined density measured value.

In a seventh embodiment of the inline measuring device of the invention, the measuring device electronics generates the monitoring value on the basis of at least one oscillation frequency serving for the monitoring, with which frequency the at least one measuring tube oscillates at least at times, and/or on the basis of a change of this at least one oscillation frequency with respect to time. In a further development of this embodiment of the invention, the measuring device electronics generates the monitoring value on the basis of a time derivative and/or another measured variable characterizing changes with respect to time of the at least one oscillation frequency serving for the monitoring.

In an eighth embodiment of the inline measuring device of the invention, the measuring device electronics compares the monitoring value with a predetermined, and/or predeterminable during operation, limit value, which represents a maximum allowable level of the monitoring value for the measuring tube during operation, and the measuring device electronics issues an alarm in the case of detected reaching and/or surpassing of the limit value.

In a ninth embodiment of the inline measuring device of the invention, the measuring device electronics compares the change of the monitoring value with respect to time with a predetermined, and/or predeterminable during operation, change limit value, which represents a maximally allowable rate of change of the monitoring value during operation, especially one averaged over a predetermined interval of time, and the measuring device electronics issues an alarm upon detected reaching and/or surpassing of the change limit value.

In a tenth embodiment of the inline measuring device of the invention, the measuring device electronics generates internally by means of the monitoring value at least one alarm signal, which signals a superelevated static internal pressure within the measurement pickup housing and/or the presence of a leak in the at least one measuring tube.

In an eleventh embodiment of the inline measuring device of the invention, the measuring device electronics communicates by means of a data transmission system, especially a hardwired fieldbus system, with a superordinated control unit processing measured values, and the measuring device electronics transmits the alarm signal to the control unit.

In a first embodiment of the method of the invention, the method further includes a step of generating, by means of the measuring device electronics, at least one monitoring value, whose level depends on the instantaneous static internal pressure within the measurement pickup housing and/or on a medium instantaneously surrounding the at least one measuring tube.

In a second embodiment of the method of the invention, the method further includes a step of comparing the at least one monitoring value with a limit value, which represents a maximally allowable level of the monitoring value for the measuring tube during operation and/or with a change limit value, which represents a maximally allowable rate of change of the monitoring value during operation, especially such averaged over a predetermined interval of time.

In a third embodiment of the method of the invention, the method further includes steps of detecting a reaching and/or surpassing of the limit value and/or the change limit value, as well as issuing of an alarm.

In a fourth embodiment of the method of the invention, the measuring device electronics determines the at least one monitoring value on the basis of at least one operating parameter internally determined and/or internally measured during operation, especially an exciter current value, which instantaneously represents an electrical current level of the exciter current, an oscillation frequency serving for the monitoring, or an operating parameter derived therefrom.

FIGS. 1a, b show an inline measuring device 1, especially one in the form of a Coriolis mass flow and/or density measuring device, which serves, for example, for registering a mass flow rate m of a medium flowing in a pipeline (not shown) and for reflecting such in a mass-flow-rate, measured-value $X_m$ instantaneously representing this mass flow rate. The medium can, in such case, be practically any flowable substance, especially a liquid, gas, vapor, or the like. Alternatively, or in supplementation thereof, the inline measuring device 1 can, as required, also be used for measuring a density, $\rho$, and/or a viscosity $\eta$ of the medium.

For the measuring of the medium, the inline measuring device 1 includes: A vibration-type measurement pickup 10, through which the medium flows during operation; and a measuring device electronics 20 electrically connected with the measurement pickup 10 and shown schematically as block 20 in FIG. 2. Advantageously, the measuring device electronics 20 is so designed, that it can, during operation of the inline measuring device 1, exchange measurement and/or other operational data with a measured value processing unit superordinated thereto, for example, a programmable logic controller (PLC), a personal computer and/or a workstation, via a data transmission system, for example, a serial fieldbus. Additionally, the measuring device electronics is so designed, that it can be fed from an external energy, or power, supply, for example also via the aforementioned fieldbus system. For the case, in which the inline measuring device is provided to be coupled to a field bus or other communication system, the, especially programmable, measuring device electronics 20 has therefor an appropriate communications interface for data communication, e.g. for the sending of the measurement and/or operational data to the already mentioned, programmable logic controller or to a superordinated process control system.

FIGS. 2 to 5 show, in various views, an example of an embodiment for the vibration-type measurement pickup 1, especially one serving as a Coriolis mass flow rate, density and/or viscosity pickup. As already mentioned, measurement pickup 1 serves for producing in a through-flowing medium such mechanical reaction forces, especially Coriolis forces as a function of mass flow rate, inertial forces as a function of density of the medium and/or frictional forces as a function of the viscosity of the medium. These forces are registerable by sensor and thus measurably affect the measurement pickup. Based on these reaction forces describing the medium, e.g. mass flow rate, density and/or viscosity of the medium can be measured by means of evaluation methods appropriately implemented in the measuring device electronics in manner known to those skilled in the art. Measurement pickup 1 is placed during operation, via flanges 2, 3, into the course of a pipeline (not shown) conveying a medium, especially a liquid, gaseous or vaporous medium, to be measured. Instead by means of flanges, measurement pickup 1 can also be connected to the mentioned pipeline by other known connecting means, such as e.g. triclamp connections or screw connections.

For conveying of the medium to be measured, the measurement pickup includes at least a first pickup tube 4, which, serving as measuring tube, is held oscillatably in a pickup housing 10, communicates during operation with the pipeline, and, driven by an electromechanical exciter arrangement 60, is caused to vibrate, at least at times, in at least one oscillation mode suited for determining the physical, measured variable. Suited as materials for the pickup tube are, especially, steel, particularly high grade, and/or stainless, steel, titanium, zirconium or tantalum. Beyond these, however, also practically any other material usually used, or, at least, suitable, therefor, can also serve for such purpose.

Besides the pickup housing 10 and the at least one pickup tube 4 held therein, the measurement pickup additionally includes an electromechanical, especially electrodynamic, exciter mechanism 60 acting on the at least one pickup tube 4 for producing and/or maintaining mechanical oscillations, especially when medium to be measured is flowing through the pickup tube 4. Additionally provided in the measurement pickup is a sensor arrangement 70 reacting to mechanical oscillations, especially bending oscillations, of the pickup tube 4, for producing at least one oscillation measurement signal $s_{vb}$ representing oscillations of the pickup tube 4. At least the at least one pickup tube, as well as the components additionally affixed thereto, such as e.g. parts of the exciter mechanism 60 and the sensor arrangement 70, form, therefore, an inner oscillation system of the measurement pickup.

During operation of the measurement pickup 1, practically the entire inner oscillation system of the measurement pickup 1, as formed by the at least one pickup tube 4 serving as measuring tube, the medium instantaneously conveyed therein, and, at least in part, by the exciter mechanism 60 and the sensor arrangement 70, executes, at least at times, mechanical oscillations having at least one, wanted oscillation frequency $F_n$, with the mechanical oscillations being developed, at least at times and/or at least in part, as lateral oscillations, especially bending oscillations. The instantaneous wanted oscillation frequency $F_n$ of the inner oscillation system is, in such case, advantageously so controlled and so tuned, that it corresponds essentially to an instantaneous, natural eigenfrequency of the inner oscillation system. As a result of this, the wanted oscillation frequency Fn depends, in manner known to those skilled in the art, both on size, shape and material of the at least one pickup tube and also, especially, on an instantaneous density of the medium. In the case of fluctuating density, especially due to changing media properties or due to changing of the medium in the pipeline system, the wanted oscillation frequency $F_n$ is, thus, variable during operation of the measurement pickup within a predetermined wanted frequency band $\Delta F_n$ having a lower limit frequency and an upper limit frequency, with the lower limit frequency corresponding to a highest expected density of the medium and the upper limit frequency arising, for example, in the case of evacuated measuring tube.

Figure 3:
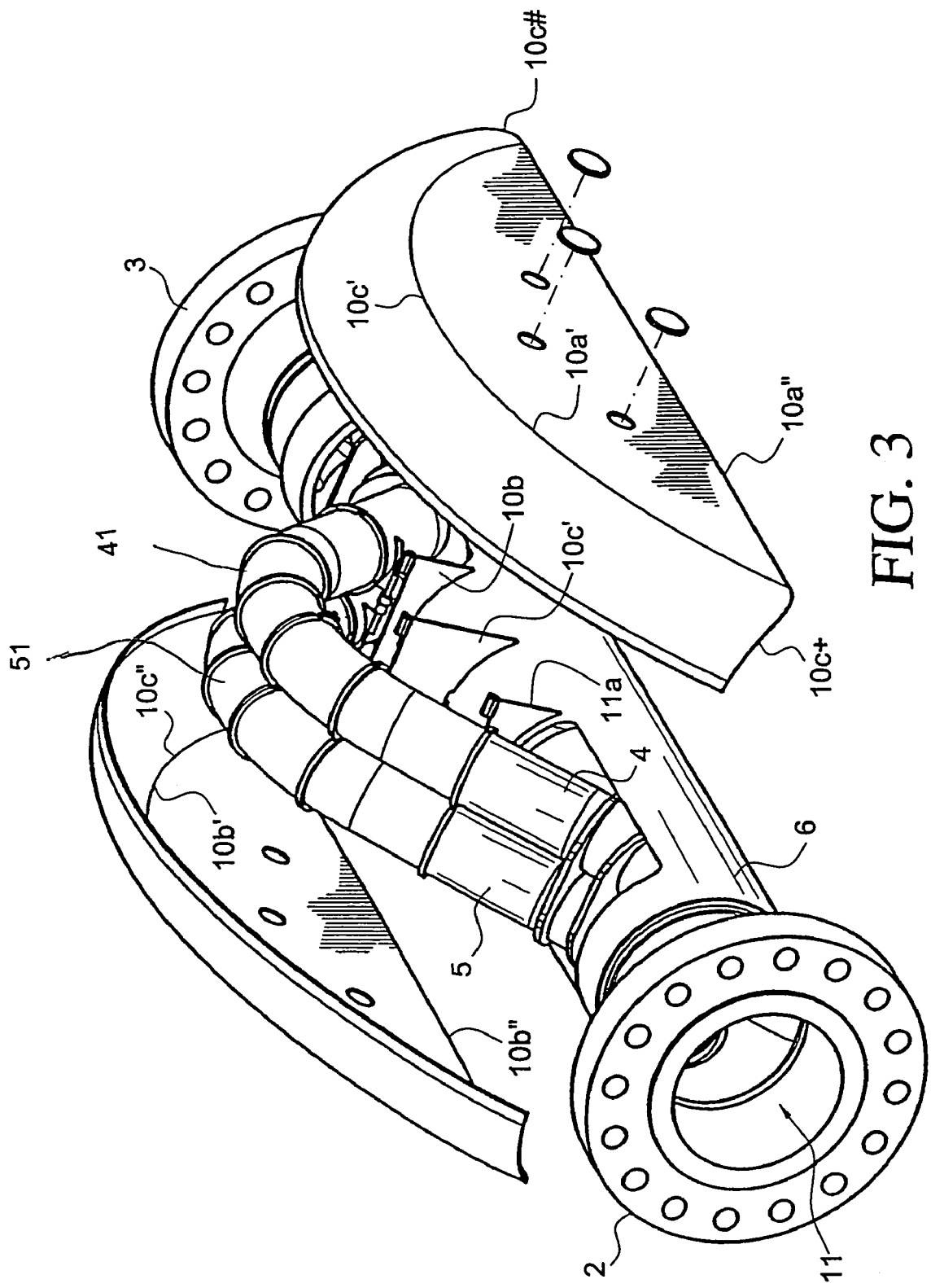
Figure 5:
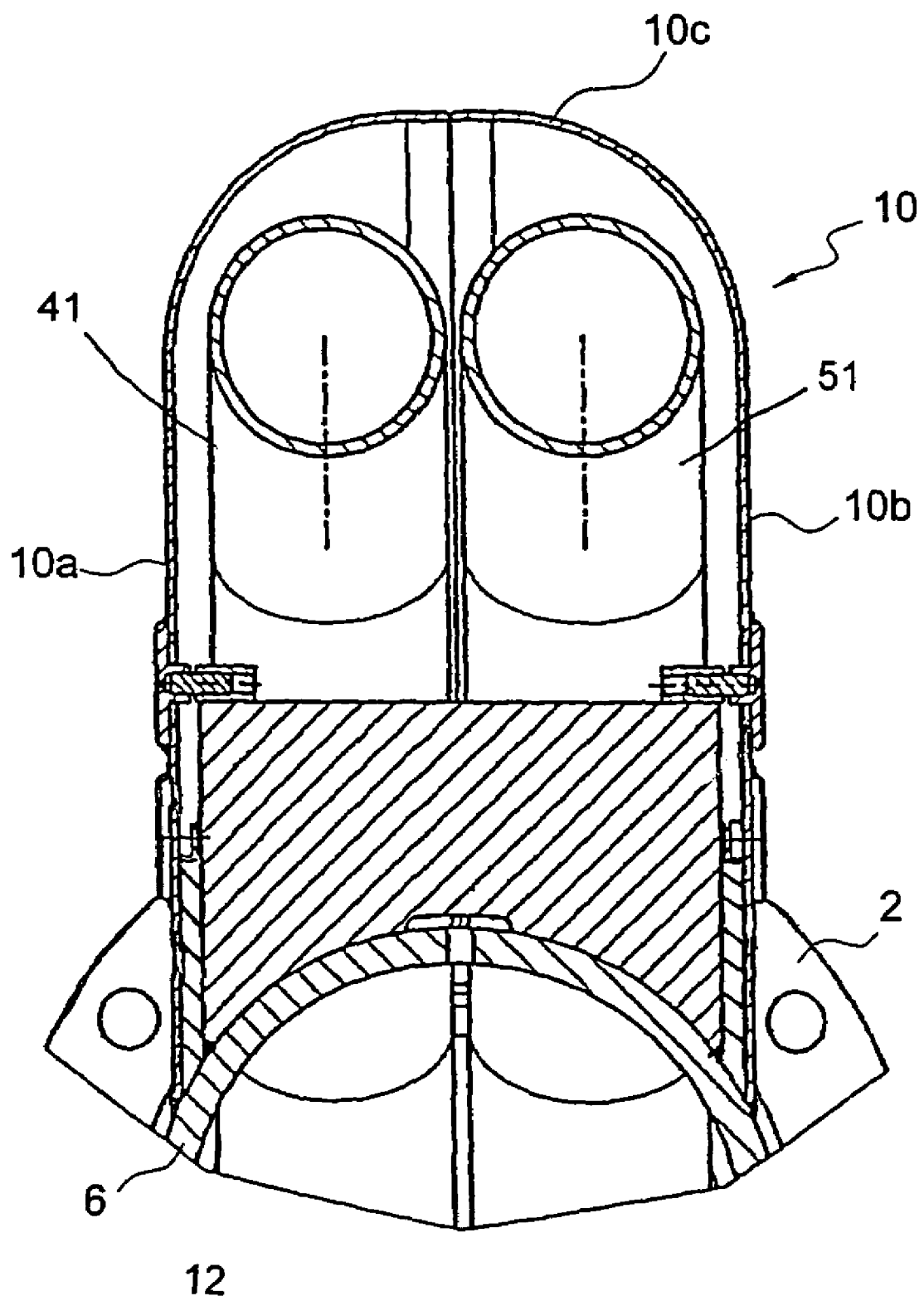

Besides the pickup tube 4, especially one formed in one piece, the example of an embodiment shown here further includes a second pickup tube 5 provided in the measurement pickup and likewise executing mechanical oscillations during operation. This second tube is essentially identical to the first pickup tube 4. Especially, the second tube likewise communicates with the pipeline and serves as a second measuring tube of the measurement pickup. The two pickup tubes 4, 5, especially ones running, at least sectionally, parallel to one another, can, as indicated in FIGS. 3 and 5, and also shown e.g. in U.S. Pat. Nos. 6,711,958, 5,796,011, 5,301,557, be connected by means of appropriate distributor pieces 11, 12 together to form flow paths flowed-through in parallel during operation; they can, however, also be connected serially together to form flow paths lying one after the other, as shown e.g. in U.S. Pat. No. 6,044,715. It is, however, also possible, as proposed, for example, in U.S. Pat. No. 6,666,098 or U.S. Pat. No. 5,549,009, to use only one of the two pickup tubes as the measuring tube serving for conveying the medium and the other as a blind tube, not flowed-through by medium to be measured and serving for reducing intrinsic imbalances in the measurement pickup.

For fine tuning of the inner oscillation system, formed by means of the two pickup tubes 4, 5, to suitable mechanical eigenfrequencies, as well as for minimizing mechanical stresses and/or vibrations caused by the vibrating pickup tubes at the inlet or outlet ends in the pickup housing, the two pickup tubes 4, 5 can, additionally, be connected mechanically together at the inlet end by means of at least one, first coupling element 217, as well as at the outlet end by means of at least one, second coupling element 218.

In the example of an embodiment shown here, each of the two pickup tubes 4, 5 has at least one central tube segment 41, 51, which is at least sectionally bent, or curved, in at least one plane. The pickup tubes 4, 5 can, in such case, as also shown in U.S. Pat. No. 6,776,052, exhibit a marked U-shape, or, as also shown in U.S. Pat. No. 6,802,224, or U.S. Pat. No. 6,711,958, be embodied in essentially V-shape or even have a trapezoidal shape. Furthermore, the pickup tubes can, however, also, as e.g. described in U.S. Pat. No. 5,796,011, be bent out only slightly, or, as shown e.g. in WO-A 01/65213, U.S. Pat. Nos. 6,308,580, 6,092,429, 6,044,715, more rectangularly or trapezoidally. As an alternative to the bent pickup tube serving as measuring tube, it is additionally also possible to use a straight tube, such as described, for example, in U.S. Pat. Nos. 4,793,191, 5,602,345, 6,006,609, 6,880,410, 6,851,323, or U.S. Pat. No. 6,840,109.

Figure 2:
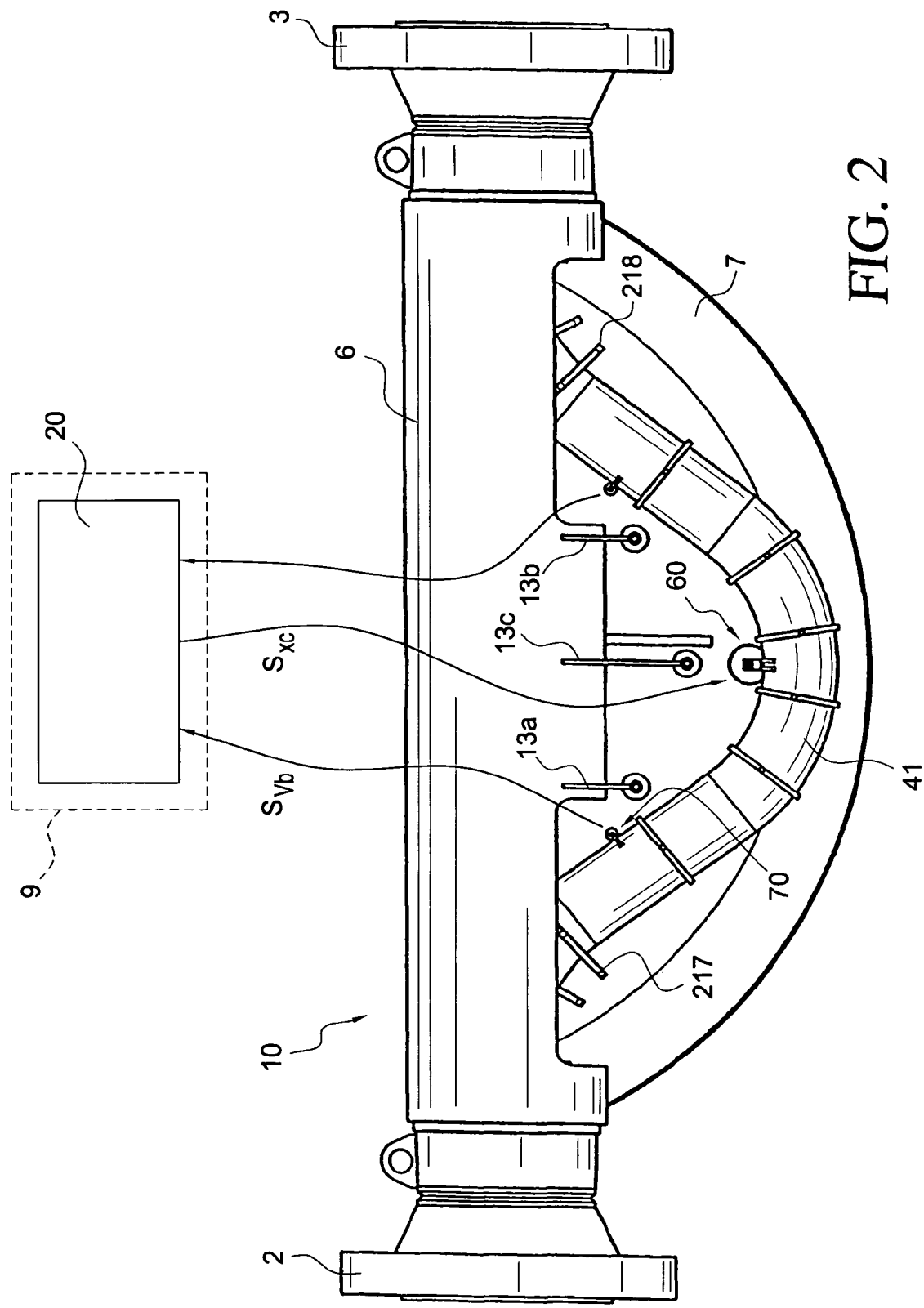
FIGS. 2 to 5 show, in different, partially sectioned, side views, details of a vibration-type measurement pickup suited for an inline measuring device of FIGS. 1a, b.

In the case of the measurement pickup illustrated in FIGS. 2 and 3, each of the two central tube segments is bent essentially in V-shape. In such case, each of the two pickup tubes 4, 5 additionally includes, at the inlet end, a straight, inlet tube segment running essentially parallel to the imaginary oscillation axis. Each of these inlet tube segments communicates, via an inlet-end, arc-shaped, intermediate tube segment, into the associated central tube segment. Additionally, each of the two pickup tubes 4, 5 also has, on the outlet end, a straight outlet tube segment running essentially parallel to the imaginary oscillation axis. Each of these outlet tube segments communicates with the associated central tube segment via an arc-shaped intermediate tube segment toward the outlet end. Furthermore, each of the central tube segments has an apex with an included angle which is smaller than 150°, especially smaller than 120°. At least the central tube segments 41, 51 of the two pickup tubes 4, 5 are excited during operation by the electromechanical exciter mechanism 60 affixed at least partially thereto, to execute cantilever-type vibrations, wherein they are laterally deflected out of the aforementioned plane and caused to oscillate essentially with mutually opposite phases. In such case, the first pickup tube and the second pickup tube execute, at least at times during operation, bending oscillations about an imaginary oscillation axis essentially parallel to a longitudinal axis L of the measurement pickup. In other words, at least the central tube segments 41, 51 are caused to oscillate in a bending oscillation mode in the manner of cantilevers clamped on one end, or the tines of a tuning fork. The exciter mechanism 60 has, in the illustrated example of an embodiment, at least one oscillation exciter arranged in each case in the region of the apexes, especially about, in each case, at the middle, on the two pickup tubes 4, 5. The oscillation exciter can be, for example, one of electrodynamic type, thus a magnet coil 62 affixed to the pickup tube 5 and an armature correspondingly affixed to the other pickup tube 4, for plunging in the magnet coil.

For registering vibrations at least of the one pickup tube 4 and for producing the at least one oscillation measurement signal $S_v$ representing oscillations of the pickup tube 4, a sensor arrangement is provided, as already mentioned. The sensor arrangement produces, in manner usual for such measurement pickups, signals representing vibrations, especially inlet end and outlet end vibrations, of the tube segment 41. Such signals can then be forwarded to an electronic further-processing. In the shown example of an embodiment, the sensor arrangement has, for such purpose, a first oscillation sensor arranged at the inlet ends of the pickup tubes 4, 5, as well as a second oscillation sensor, especially one essentially identical or of equal construction to the first oscillation sensor, arranged at the outlet ends of the pickup tubes 4, 5. The oscillation sensors can likewise be those of electrodynamic type, thus implemented in each case by means of a magnet coil affixed to the pickup tube 5 and an armature affixed correspondingly to the other pickup tube 4 for plunging in the magnet coil. However, also other oscillation sensors known to those skilled in the art can be used as oscillation sensors, an example being opto-electronic oscillation sensors.

Figure 4:
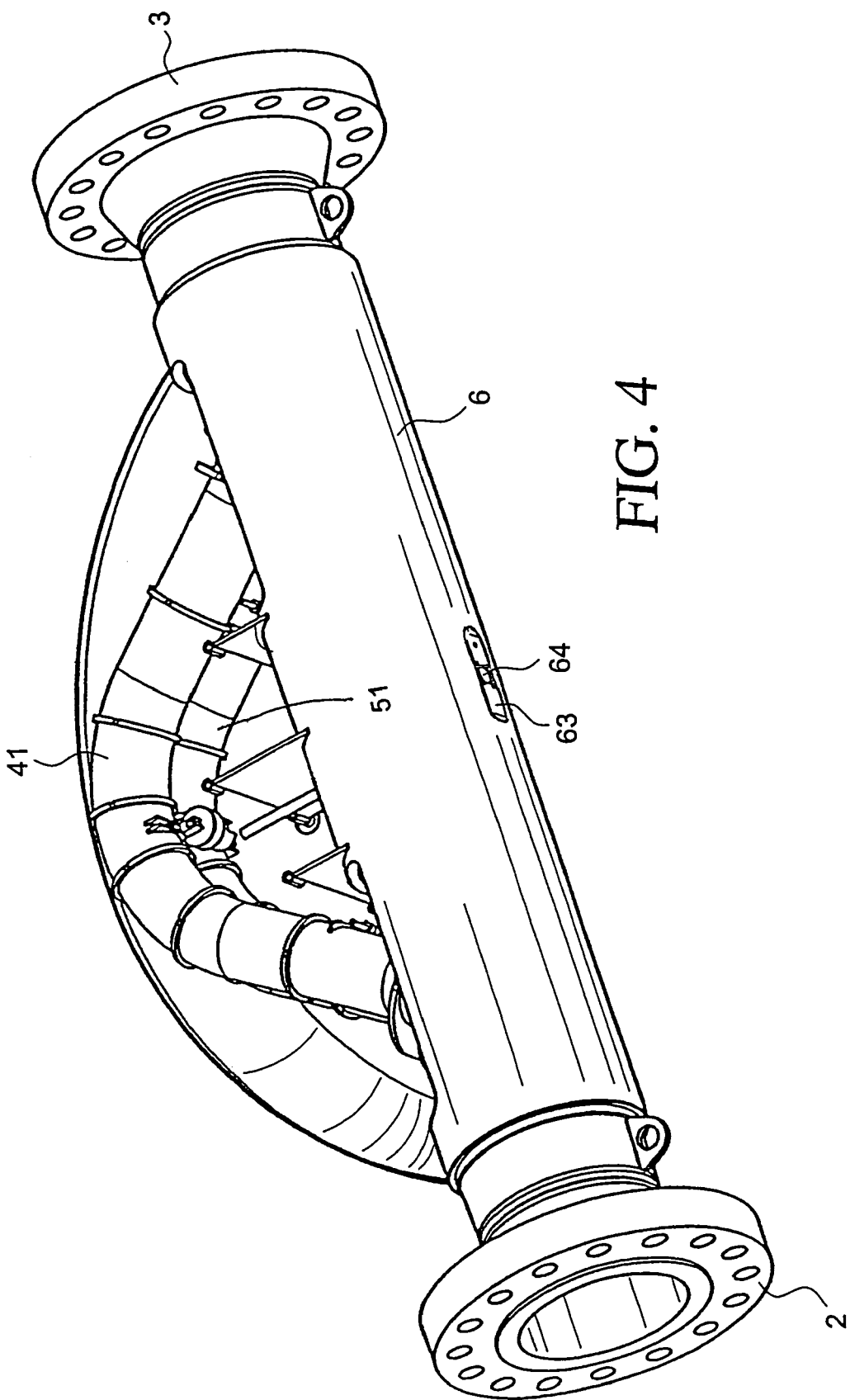
Figure 6:
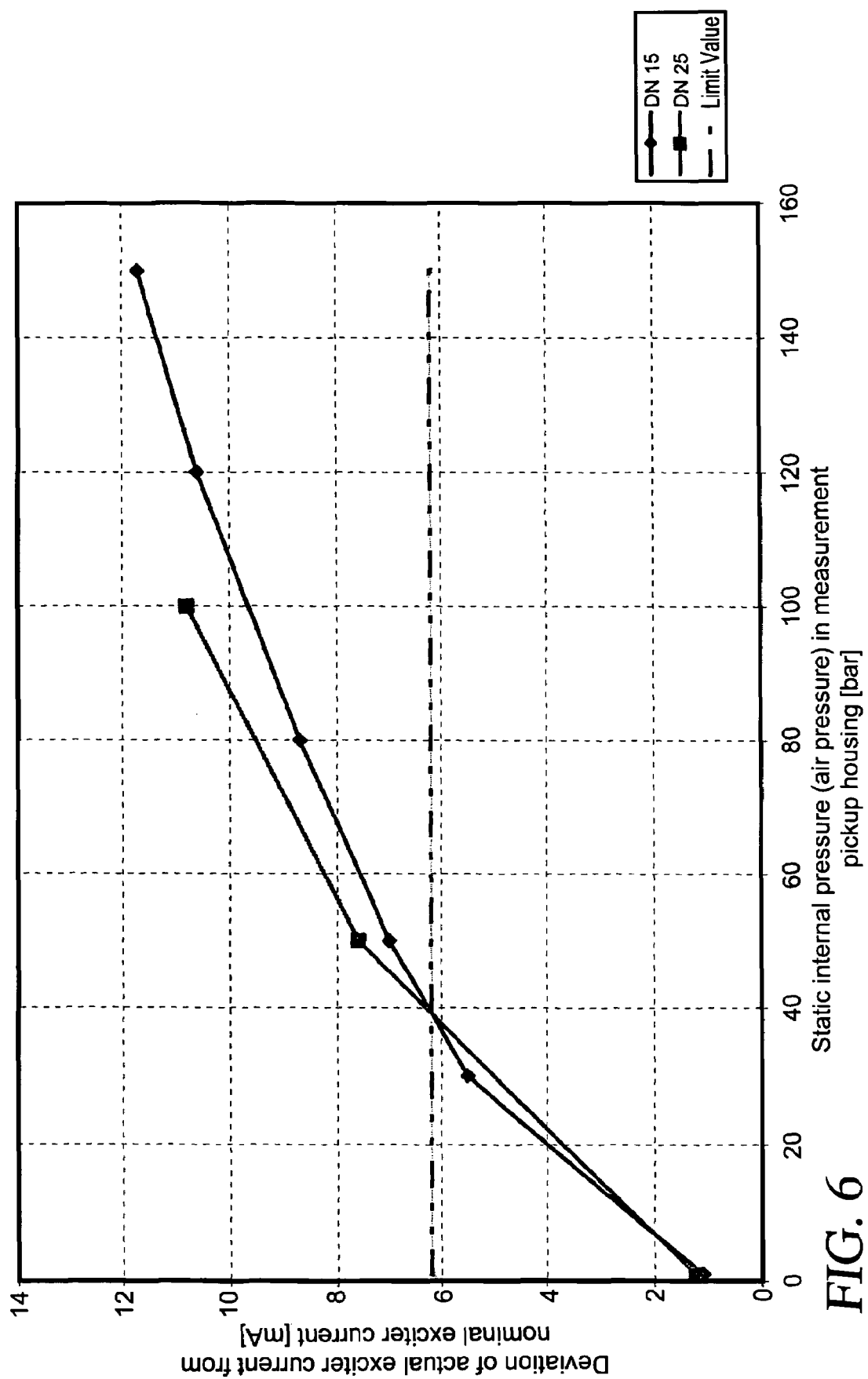
FIG. 6 shows experimentally determined plots of deviation of exciter current driving vibration-type measurement pickups from nominal exciter currents determined initially for measurement pickups according to FIGS. 1a, b having different specified diameters, as a function of internal pressure in the measurement pickup housings thereof.

For determining the at least one physical, measured variable on the basis of the at least one oscillation measurement signal $s_{vb}$, the exciter mechanism 60 and the sensor arrangement 70 are, as usual for measurement pickups of such type, electrically connected in suitable manner, for example galvanically and/or inductively and/or opto-electronically coupled, with a measuring and operating circuit appropriately provided in the measuring device electronics 20. The measuring and operating circuit, in turn, produces, on the one hand, a driver signal $s_{xc}$ appropriately driving the exciter mechanism 60, for example controlled with respect to an exciter current and/or an exciter voltage. As a result of this, an exciter current appropriately delivered from the measuring device electronics 20 is caused to flow through the exciter mechanism, where this current is converted by means of the at least one oscillation exciter into the exciter forces causing the at least one measuring tube to vibrate. On the other hand, the measuring and operating circuit receives the at least one oscillation measurement signal $s_{vb}$ of the sensor arrangement 70 and generates therefrom desired measured values, which can represent, for example, a mass flow rate, a density and/or a viscosity of the medium to be measured and which can, as required, be displayed on-site or also as required, be further processed at a higher level. The measuring device electronics 20, including the measuring and operating circuit, can be accommodated, for example, in a separate electronics housing 9, which can be arranged remotely from the measurement pickup or, in the sense of providing a single, compact, inline measuring device, it can be affixed directly on the measurement pickup 1, for example externally on the measurement pickup housing 10. In the case of the example of an embodiment shown here, a neck-like transition piece 8 is attached for this on the pickup housing to serve for holding the electronics housing 9. In FIGS. 1a, 6, the transition piece 8 and the electronics housing 9 are, however, omitted; only in FIG. 4 is a seating surface 63 shown recessed into a wall of the pickup housing 10 for receiving the transition piece 8. The seating surface 63 is provided with an electric feedthrough 64, by means of which the electrical connections for the exciter mechanism 60 and the sensor arrangement 70, as well as other electric components, such as e.g. pressure and/or temperature sensors provided, as required, in the measurement pickup 1, can The pickup tubes 4, 5 of the measurement pickup, along with also the exciter mechanism and sensor arrangement attached, in each case, thereto, are, as evident, without more, from the combination of FIGS. 1a, 3 and 5, practically completely encased by the already mentioned pickup housing 10. The pickup housing 10 serves, in this respect, thus not only as holder of the at least one pickup tube 4, but also, beyond this, also for protecting the internally situated components of the measurement pickup 1, such as e.g. the exciter mechanism and sensor arrangement and possibly, in addition, other components of the measurement pickup placed within the pickup housing, against environmental influences, such as e.g. dust or water spray. Additionally, the pickup housing can, furthermore, also be so embodied and so dimensioned, that it can, up to a required maximum excess pressure in the interior of the pickup housing, retain, as completely as possible, medium escaping from the pickup tube 4 in the case of possible damage thereto, e.g. due to crack formation or bursting. Examples of material for the pickup housing, especially also the housing cap 7, include e.g. steels, such as structural steel or stainless steel, or other suited, high-strength materials. In a further embodiment of the measurement pickup, the pickup tube 4, especially one at least sectionally bent, and the pickup housing are both made of the same material, especially steel or high-grade steel, such as a high-grade stainless steel, or at least of materials similar to one another, especially different types of steel. Furthermore, it is provided that the flanges are, as illustrated in FIGS. 1a, b, and as is quite usual in the case of measurement pickups of such type, embodied as integral components of the pickup housing, in order, in this way, to achieve as short installed lengths as possible, coupled with as high stability as possible for the measurement pickup; equally, it is also possible to integrate the possibly provided distributor pieces 11, 12 directly into the pickup housing.

In the example of an embodiment shown here, the pickup housing 10 includes a support element 6 (illustrated here as a laterally at least partially open, support cylinder), which, as presented in FIGS. 3 to 5, is so mechanically connected on the inlet and outlet ends with the at least one pickup tube, that the at least one bent tube segment 41 projects laterally out of the support element. Additionally, the pickup housing has a housing cap 7 arranged spaced from the bent central tube segments of the pickup tubes 4, 5 and affixed to the support element 6, especially durably and/or so as to be impenetrable to the medium. In the case of the example of an embodiment illustrated here, at least the pickup tube 4 is so held in the, here, tubular support element 6 at the inlet and outlet ends, that the oscillatable central tube segment, running through two cutouts of the support element 6, projects laterally out of the support element and, therefore, into the housing cap 7 likewise affixed to the support element 6. It is, in such case, still to be mentioned, that, instead of the here more tubularly illustrated support element 6, also, an, as required, solid support cylinder with another suitable cross section can be used, for example a support element embodied more in the form of a beam. The housing cap 7 serving for the housing of the tube segment 41 includes, as illustrated schematically in FIGS. 3 and 5 a trough-shaped cap segment 10c as well as essentially planar, first and second lateral housing segments 10a, 10b. The second lateral housing segment is essentially mirror symmetrical to the first lateral housing segment. The shape of cap segment 10c corresponds, as evident, without more, from the combination of FIGS. 3a and 3b, essentially to that of a toroidal shell. Accordingly, the cap segment 10c has an essentially circular arc-shaped, preferably semicircularly shaped, cross section of predeterminable radius r and, at least virtually, an essentially circular arc-shaped, first segment edge 10c' having a radius R essentially greater in comparison with radius r, as well as a second segment edge 10c" formed essentially identically to the first segment edge. If necessary, both the cross section as well as also the segment edges, need not be perfectly circular, thus they can be formed slightly elliptically, for instance. As evident, without more, from the combination of FIGS. 1a, b and 3, the lateral housing segments 10a, 10b are each connected via circular arc-shaped, first segment edges, respectively 10a', 10b', with the first and second segment edges 10c', 10c''', respectively, of the cap segment 10c, and, indeed, in such a manner, that the lateral housing segments 10a, 10b each are oriented essentially in alignment with tangential planes of the cap segment 10c and, therefore, with tangents to the associated segment edges 10ca, 10cb. In other words, between the cap and housing segments 10c, 10a, and the cap and housing segments 10c, 10b, in each case, there is a largely continuous, thus as smooth as possible, transition, in which, in the case of allowable internal excess pressure, little or no bending stresses are produced. Moreover, the housing cap 7 is affixed to the support element 6 via a third segment edge 10c+ and a fourth segment edge 10c# of the cap segment 10c, as well as via, in each case, a second segment edge 10a'', 10b'' of the first and second lateral housing segments 10a and 10b, and, indeed, in such a manner, that the cap segment 10c and the housing segments 10a, 10b remain spaced during operation from the at least one vibrating tube segment 41. For manufacturing the housing cap 7, the segments 10c, 10a, 10b can be e.g., in each case, prefabricated and then subsequently joined together, especially by means of welding. Advantageously, the method for the manufacture of a metal cap usable as housing cap 7 described in the already mentioned WO-A 03/021202 can be applied in the manufacture of the housing cap 7. In such method, the metal cap is formed by welding two essentially identically shaped cap halves, especially such cut out of a dish-shaped stock, having an edge bead, especially a quarter-torus-shaped edge bead. Additionally, the housing cap 7 can be deep drawn from sheet metal of appropriate thickness.

As already mentioned, the measuring device electronics 20 produces during operation, on the one hand, the driver signal feeding the exciter mechanism, while, on the other hand, the measuring device electronics receives the oscillation signals of the sensor arrangement and generates therefrom desired measured values representing mass flow rate, density, viscosity or temperature of the flowing fluid. According to the invention, it is further provided that the measuring device electronics monitors during operation a static internal pressure within the measurement pickup housing and/or a hermeticity of the at least one measuring tube. For this purpose, the measuring device electronics determines, in an advantageous embodiment of the invention, at least one monitoring value repeatedly on the basis of at least one operating parameter determined, or updated, as the case may be, internally of the measuring device electronics. The level of the monitoring value is a function of the instantaneous static internal pressure within the measurement pickup housing and/or of a medium instantaneously surrounding the at least one measuring tube. For the above mentioned case in which the measuring device electronics communicates by means of the data transmission system with a superordinated control unit, which processes measured values, the measuring device electronics can, for example, send the alarm signal via the data transmission system also to the control unit.

In a further embodiment of the invention, it is additionally provided that the measuring device electronics compares the monitoring value with a limit value, which represents a maximally allowable level of the monitoring value for the measuring tube during operation and/or that the measuring device electronics compares the monitoring value with a change limit value, which represents a maximally allowable rate of change (especially one averaged over a predetermined interval of time) of the monitoring value during operation. For the case in which the measuring device electronics detects a reaching and/or surpassing of the limit value or the change limit value, a corresponding alarm is issued from the measuring device electronics. The limit value, or change limit value, as the case may be, can be data values determined initially, for example during calibration and/or at startup of the inline measuring device; however, if required, the limit value, or the change limit value, can also be changed by the user, for example even via the data communication system, during operation of the inline measuring device and, therefore, matched in real time to the actually existing conditions, for example, the kind, or characteristics, of the medium being measured at the moment.

Further investigations have shown that, in such case, both the driver signal for the exciter mechanism and also the at least one oscillation measurement signal can provide information concerning the static internal pressure to be monitored within the measurement pickup housing and, therefore, also concerning the hermeticity to be monitored for the at least one measuring tube. Accordingly, the operating parameter internally determined and/or internally measured during operation can, for example, be the exciter current, the instantaneously excited, wanted oscillation frequency, an instantaneous damping of the oscillating measuring tube and/or parameters derived therefrom, such as e.g. the density, $\rho$, instantaneously measured by means of the measuring device electronics and/or the viscosity, $\eta$, of the medium, as measured by means of the measuring device electronics. Thus, it was determined, for instance, that a deviation of the exciter current, which is easily measurable during operation, from an exciter current nominally expected during normal operation shows a very strong, almost proportional, dependence on the instantaneous static internal pressure. Corresponding plots of exciter current, or its deviation from the nominal exciter current, as experimentally determined, by way of example, on the basis of two essentially equally constructed measurement pickups of differing nominal diameters (DN 15, DN 25) and for different internal pressures in the measurement pickup housing, are presented in FIG. 6.

Accordingly, provided in a further embodiment of the invention is that the measuring device electronics generates the monitoring value from the at least one driver signal, especially on the basis of the exciter current flowing in the exciter mechanism and/or on the basis of a change of the exciter current with respect to time. To this end, in a further, advantageous embodiment of the invention, the measuring device electronics determines, at least at times, internally, an exciter current value, especially a digital one, which represents an instantaneous electrical current level of the exciter current, which is then also used for generating the monitoring value. If necessary, also a series and/or a time average of a plurality of exciter current values, especially digitally stored ones, serve for producing the monitoring value. Alternatively, or in supplementation, also a derivative of the electrical current level of the exciter current with respect to time and/or another measured value characterizing time changes of the electrical current level of the exciter current, for example the reciprocal of the derivative with respect to time and/or a time averaged value, can be drawn upon for determining the monitoring value. Beyond this, instead of absolute values for the exciter current or its instantaneous deviation from the nominal exciter current, also relative values for the deviations and, to such extent, also for the determining of the monitoring value, can be used.

Figure 7:
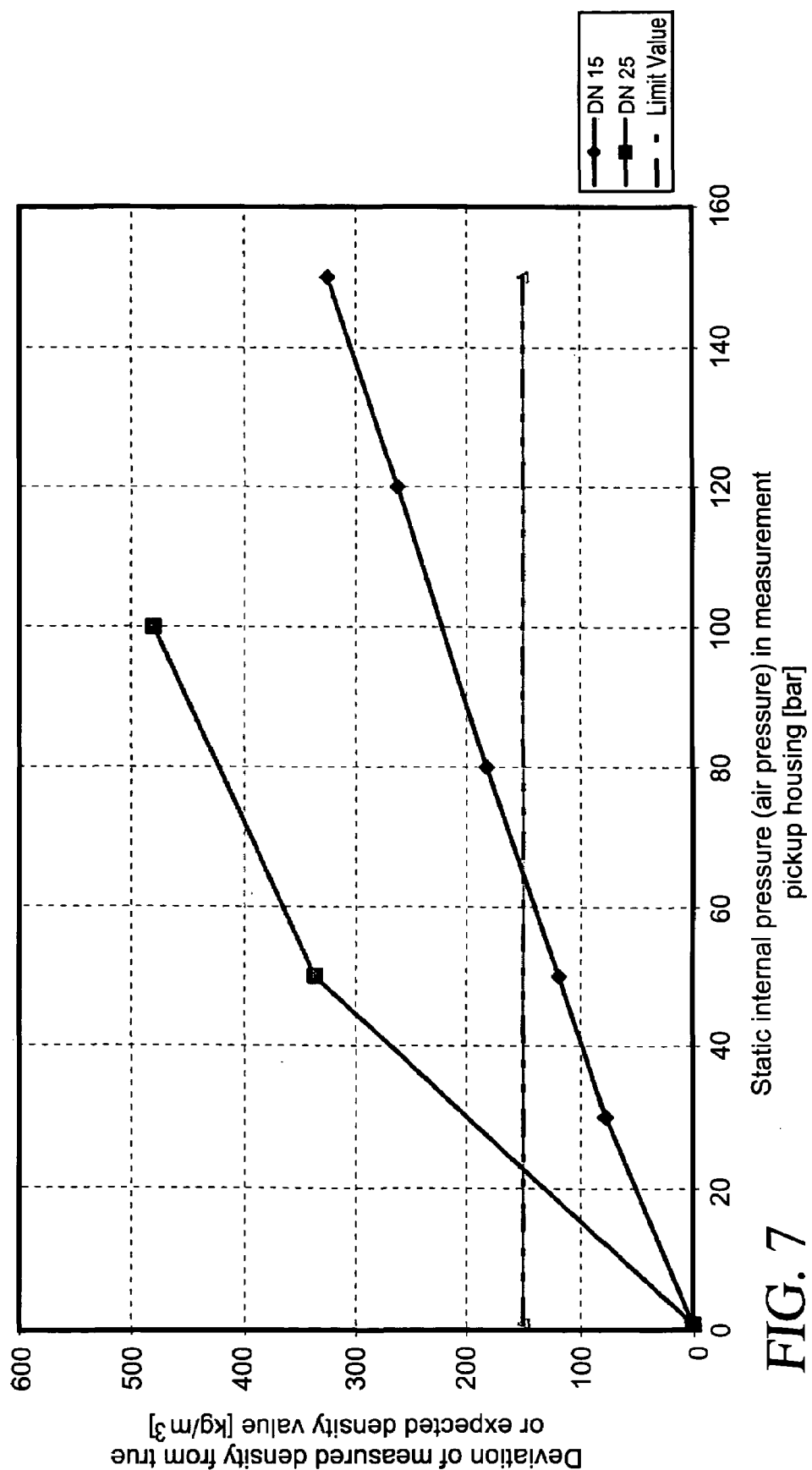
FIG. 7 shows experimentally determined plots of deviations of density from a predetermined reference density, as measured by means of vibration-type measurement pickups according to FIGS. 1a, b of different specified diameters, as a function of internal pressure in the measurement pickup housings thereof.

It was additionally possible to determine that, besides the exciter current, also the density, $\rho$, measured based on the oscillation measurement signal, especially on the basis of the wanted oscillation frequency, reacts equally significantly to an increasing of the static internal pressure in the measurement pickup housing with a corresponding deviation from a nominal, reference density. Experimentally determined curves showing measured density, or its deviation from a predetermined reference density, are presented in FIG. 7, by way of example, as a function of the internal pressure measured within the measurement pickup housing. Accordingly, the measuring device electronics in a further development of the invention is further provided for measuring the density, $\rho$, of the medium and for delivering, at least at times, a density measured value $X_\rho$, especially a digital one, representing the density, $\rho$, of the medium. In such case, the measuring device electronics is additionally designed for generating the monitoring value from the internally determined density measured value $X_\rho$, especially on the basis of a series of digitally stored density measured values. Alternatively, or in supplementation thereof, also a derivative of the measured density with respect to time and/or another measured value characterizing time changes of the measured density can serve for determining the monitoring value. It is to be noted here, further, that, instead of the measured density, also the oscillation frequency dependent on the density of the medium and with which the at least one measuring tube oscillates, at least at times, can be drawn-upon for generating the monitoring value, especially since the wanted oscillation frequency excited during operation is determined at least for the control of the driver signal as well as also, as required, for the purpose of density measurement anyway. Equally, therefore, measured values additionally also generated from the at least one oscillation frequency can be used for generating the monitoring value, for example, time changes, or other measured variables characterizing time changes of the at least one oscillation frequency. The limit value can, in such case, correspond, for example, with the above-mentioned, lower limit frequency of the wanted frequency band $\Delta F_n$, while the change limit value can be determined initially, for example, on the basis of a maximally allowable rate of change for the wanted oscillation frequency for the measurement pickup. Also, in the case of using the measured density, or the measured oscillation frequency, as the case may be, the monitoring value can likewise be based both on absolute as well as on relative values for the instantaneous deviations from the relevant nominal value.

Figure 8:
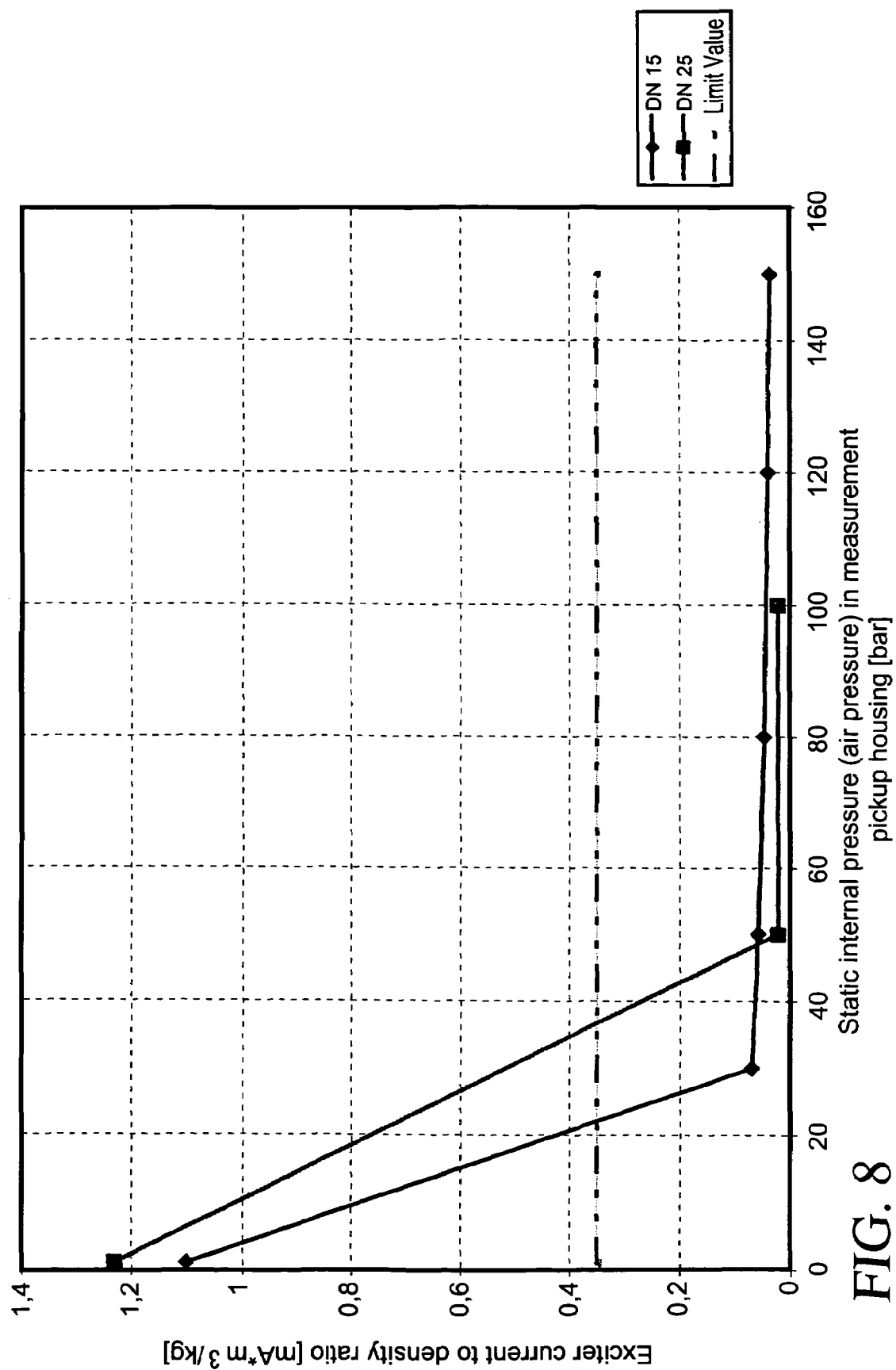
FIG. 8 shows plots of exciter currents of FIG. 6 normalized on the basis of the associated measured density measured values of FIG. 7.

In a further embodiment of the invention, it is provided that the measuring device electronics determines the monitoring value both on the basis of the exciter current and on the basis of the internally determined density measured value and/or the at least one internally measured oscillation frequency of the measuring tube. Proving to be an especially advantageous operational parameter for this is, for example, a quotient formed by means of the internally determined, exciter current value and the internally determined, density measured value, wherein through use of the above-mentioned, experimentally determined measurement data for each of the exciter current and the density, the curves shown in FIG. 8 result for the exciter currents normalized on the associated measured density measured values. Clearly recognizable is the initially very steep decline of the correspondingly normalized exciter current, which leads thereto, that, already at very slight and rather uncritical pressure increases in the region below 100 bar, a simple and robust detecting of abnormally increased, leakage-caused, static internal pressure existing in the measurement pickup housing is made possible.

Due to the intrinsic monitoring also of the static internal pressure within the measurement pickup housing as well as also of the hermeticity of the at least one measuring tube, the inline measuring device of the invention is especially suited also for use in pipeline systems conveying potentially environmentally endangering, especially toxic and/or explosive, media. Beyond this, the inline measuring device of the invention can also be used advantageously in pipeline systems conveying fluids during operation at high pressure of far in excess of 200 bar. Of special advantage is the self-actuating monitoring of the internal pressure in the measurement pickup housing by means of the measuring device electronics, moreover, for inline measuring devices, whose measurement pickup housing is, as is the case, for example, often for the above-mentioned support cylinder, built relatively thick-walled, and, in such respect, also relatively capable in resisting pressure, since, then, on the one hand, a pressure increase inside is scarcely noticeable from the outside and, on the other hand, a possible bursting of the measurement pickup housing would lead to catastrophic destruction within the affected plant, due then to the inherent very high level of stored mechanical energy.

The invention claimed is:

1. An inline measuring device for measuring a medium flowing in a pipeline, said inline measuring device comprising:
    a vibration-type measurement pickup; and
    measuring device electronics electrically coupled with said vibration-type measurement pickup, wherein:
    said vibration-type measurement pickup includes at least one measuring tube vibrating during operation and communicating with the pipeline, an electromechanical exciter mechanism acting on said at least one measuring tube for producing and maintaining mechanical oscillations of said at least one measuring tube, a sensor arrangement for producing at least one oscillation measurement signal representing oscillations of said at least one measuring tube, and a measurement pickup housing housing said at least one measuring tube together with said exciter mechanism and said sensor arrangement;
    said measuring device electronics monitors a static internal pressure within said measurement pickup housing and/or monitors a hermeticity of said at least one measuring tube,
    said measuring device electronics repeatedly determines at least one monitoring value on the basis of at least one operational parameter internally determined and/or internally measured during operation, and
    said measuring device electronics generates internally at least one alarm signal by means of said monitoring value, said alarm signal signalling a superelevated static internal pressure within said measurement pickup housing and/or said alarm signal signalling the presence of a leak in said at least one measuring tube.

2. The inline measuring device as claimed in claim 1, wherein:
    a level of the monitoring value is a function of the instantaneous static internal pressure within said measurement pickup housing and/or of a medium instantaneously surrounding said at least one measuring tube.

3. The inline measuring device as claimed in claim 2, wherein:
    a level of the monitoring value is a function of the instantaneous static internal pressure within said measurement pickup housing.

4. The inline measuring device as claimed in claim 3, wherein:
    the level of the monitoring value also is a function of a medium instantaneously surrounding said at least one measuring tube.

5. The inline measuring device as claimed in claim 2, wherein:
    a level of the monitoring value is a function of a medium instantaneously surrounding said at least one measuring tube.

6. The inline measuring device as claimed in the claim 1, wherein:
    said measuring device electronics generates the monitoring value from said at least one oscillation measurement signal.

7. The inline measuring device as claimed in the claim 1, wherein:
    said measuring device electronics produces at least one driver signal for said exciter mechanism; and said measuring device electronics generates the monitoring value from said at least one driver signal.

8. The inline measuring device as claimed in claim 7, wherein:
    said electromechanical exciter mechanism of the transducer is an electrodynamic exciter mechanism.

9. The inline measuring device as claimed in the claim 1, wherein:
    said exciter mechanism is flowed-through, at least at times, by an exciter current driven by said measuring device electronics; and said measuring device electronics generates the monitoring value on the basis of said exciter current and/or on the basis of a change of said exciter current with respect to time.

10. The inline measuring device as claimed in claim 9, wherein:
    said measuring device electronics determines an exciter electrical current value, which instantaneously represents an electrical current level of said exciter current; and said measuring device electronics generates the monitoring value from at least one internally determined exciter current value.

11. The inline measuring device as claimed in claim 10, wherein:
    said measuring device electronics generates the monitoring value on the basis of a series of exciter current values.

12. The inline measuring device as claimed in claim 11, wherein:
    said measuring device electronics generates the monitoring value on the basis of a derivative of the electrical current level of the exciter current with respect to time and/or on the basis of another measured variable characterizing changes of the electrical current level of said exciter current with respect to time.

13. The inline measuring device as claimed in claim 10, wherein:
    said measuring device electronics generates the monitoring value on the basis of a series of exciter current values.

14. The inline measured variable as claimed in claim 9, wherein:
    said measuring device electronics generates said monitoring value on the basis of a quotient formed by means of an internally determined, exciter current value and an internally determined, density measured value.

15. The inline measuring device as claimed in claim 9, wherein:
    said measuring device electronics determines an digital exciter electrical current value, which instantaneously represents an electrical current level of said exciter current; and said measuring device electronics generates the monitoring value from at least one internally determined exciter current value.

16. The inline measuring device as claimed in claim 1, further adapted for measuring a density of the medium, wherein:

said measuring device electronics uses said at least one oscillation measurement signal to determine, repeatedly, a density measured value, which represents, instantaneously, a density of the medium; and said measuring device electronics generates said monitoring value from at least one internally determined density measured value.

17. The inline measuring device as claimed in claim 16, wherein:
said measuring device electronics generates said monitoring value on the basis of a series of density measured values.

18. The inline measuring device as claimed in claim 17, wherein:
said measuring device electronics generates said monitoring value on the basis of a time derivative of the measured density and/or on the basis of another measured variable characterizing changes of the measured density with respect to time.

19. The inline measuring device as claimed in claim 16, wherein:
said measuring device electronics determines the density measured value on the basis of said at least on oscillation frequency serving for the monitoring.

20. The inline measuring device as claimed in claim 16, wherein:
said measuring device electronics generates said monitoring value on the basis of a series of density measured values.

21. The inline measuring device as claimed in claim 16, wherein;
said measuring device electronics generates said monitoring value on the basis of a series of digitally stored density measured values.

22. The inline measuring device as claimed in claim 1, wherein:
said measuring device electronics generates said monitoring value on the basis of at least one monitoring-serving oscillation frequency, with which said at least one measuring tube oscillates at least at times, and/or on the basis of a change of this at least one oscillation frequency with respect to time.

23. The inline measuring device as claimed in claim 22, wherein:
said measuring device electronics generates said monitoring value on the basis of a derivative with respect to time and/or on the basis of another measured variable characterizing time changes of said at least one oscillation frequency serving for the monitoring.

24. The inline measuring device as claimed in the claim 1, wherein:
said measuring device electronics compares said monitoring value with a limit value representing a maximally allowable level of said monitoring value for the measuring tube during operation.

25. The inline measuring device as claimed in the claim 24, wherein:
said limit value is predetermined; and/or said change limit value is predeterminable during operation.

26. The inline measuring device as claimed in the claim 24, wherein:
said measuring device electronics issues an alarm upon detecting the reaching of said limit value; and/or
said the measuring device electronics issues an alarm upon detecting the surpassing of said limit value.

27. The inline measuring device as claimed in the claim 1, wherein:

said measuring device electronics compares the change of said monitoring value with respect to time with a change limit value, representing a maximally allowable rate of change of the monitoring value during operation.

28. The inline measuring device as claimed in claim 27, wherein:
said measuring device electronics issues an alarm upon detecting reaching and/or surpassing of the change limit value.

29. The inline measuring device as claimed in claim 28, wherein:
said measuring device electronics communicates, via a data transmission system, with a superordinated control unit processing measured values, and said measuring device electronics sends the alarm signal to the control unit.

30. The inline measuring device as claimed in claim 29, wherein:
said data transmission system is a hardwired fieldbus system.

31. The inline measuring device as claimed in the claim 27, wherein:
said change limit value is predetermined; and/or said change limit value is predeterminable during operation.

32. The inline measuring device as claimed in the claim 27, wherein:
said measuring device electronics issues an alarm upon detecting reaching of said change limit value; and/or
said measuring device electronics issues an alarm upon detecting surpassing of said change limit value.

33. The inline measuring device as claimed in the claim 1, wherein:
said measuring device electronics produces at least one driver signal for said exciter mechanism; and said measuring device electronics generates the monitoring value from on the basis of the exciter current flowing in said exciter mechanism.

34. The inline measuring device as claimed in the claim 1, wherein:
said measuring device electronics compares the change of said monitoring value with respect to time with a change limit value, representing a maximally allowable rate of change of the monitoring value during operation, said rate of change being averaged over a predetermined interval of time.

35. A method for monitoring an inline measuring device for measuring a medium flowing in a pipeline, which inline measuring device includes measuring device electronics, as well as a vibration-type measurement pickup electrically coupled therewith, the measurement pickup including at least one measuring tube communicating with the pipeline and vibrating during operation, an electromechanical exciter mechanism acting on the at least one measuring tube for producing and maintaining mechanical oscillation of the measuring tube, a sensor arrangement for producing at least one oscillation measurement signal representing oscillations of the measuring tube and having at least one oscillation sensor arranged on the measuring tube or in its vicinity, and a measurement pickup housing housing the at least one measuring tube together with the exciter mechanism and the sensor arrangement, said method comprising the steps of:
causing the medium to be measured to flow through the at least one measuring tube of the measurement pickup;
causing an exciter current delivered by the measuring device electronics to flow through the exciter mechanism and causing the at least one measuring tube to vibrate, in order to produce reaction forces in the medium, which forces correspond to at least one measured variable to be registered for the medium;

registering vibrations of the at least one measuring tube by means of the sensor arrangement and producing at least one oscillation measurement signal representing mechanical oscillations of the measuring tube for determining a static, internal pressure within the measurement pickup housing and/or monitoring a hermeticity of the at least one measuring tube;

generating, by means of the measuring device electronics, at least one monitoring value, whose level is a function of an instantaneous static internal pressure within the measurement pickup housing and/or of a medium instantaneously surrounding the at least one measuring tube; as well as comparing said at least one monitoring value with a limit value, which represents a maximally allowable level of the monitoring value for the measuring tube during operation, and/or comparing said at least one monitoring value with a change limit value, which represents a maximally allowable rate of change of the monitoring value during operation.

36. The method as claimed in claim 35, further comprising: at least on of the following steps:

detecting a reaching of the limit value by said monitor value;

detecting a surpassing of the limit value by said monitor value;

detecting a reaching of the change limit value by said monitor value; and detecting a surpassing of the change limit value by said monitor value.

37. The method as claimed in claim 36, further comprising at least on of the following steps:

issuing an alarm signalling reaching of the limit value by said monitor value;

issuing an alarm signalling surpassing of the limit value by said monitor value;

issuing an alarm signalling reaching of the change limit value by said monitor value; and issuing an alarm signalling surpassing of the change limit value by said monitor value.

38. The method as claimed in claim 35, wherein:

the measuring device electronics determines the at least one monitoring value on the basis of an exciter current value, instantaneously representing an electrical current level of the exciter current; and/or the measuring device electronics determines said at least one monitoring value on the basis of an oscillation frequency of the at least one measuring tube.

39. The method as claimed in claim 35, wherein:

the measuring device electronics determines the at least one monitoring value on the basis of an operational parameter derived from an exciter current value, instantaneously representing an electrical current level of the exciter current; and/or the measuring device electronics determines the at least one monitoring value on the basis of an operational parameter derived from an oscillation frequency serving of the at least one measuring tube.

40. The method as claimed in claim 35, wherein:

said measuring device electronics determines the at least one monitoring value on the basis of at least one operational parameter internally determined during operation; and/or said measuring device electronics determines the at least one monitoring value on the basis of at least one operational parameter internally measured during operation.

41. The method as claimed in claim 35, wherein:

said medium flowing through the pipe is gaseous and/or liquid.

* * * * *